(12) United States Patent
Bornhoft

(10) Patent No.: US 8,915,891 B2
(45) Date of Patent: Dec. 23, 2014

(54) INTEGRATED CATHETER SECUREMENT AND LUER ACCESS DEVICE

(75) Inventor: Stephen Bornhoft, Midvale, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 176 days.

(21) Appl. No.: 13/615,201

(22) Filed: Sep. 13, 2012

(65) Prior Publication Data
US 2014/0074031 A1 Mar. 13, 2014

(51) Int. Cl.
*A61M 5/00* (2006.01)
*A61M 25/06* (2006.01)
*A61M 39/10* (2006.01)
*A61M 25/02* (2006.01)

(52) U.S. Cl.
CPC ........... *A61M 25/0606* (2013.01); *A16M 5/158* (2013.01); *A61M 25/0631* (2013.01); *A61M 39/10* (2013.01); *A61M 2039/1066* (2013.01); *A61M 2039/1072* (2013.01); *A61M 2025/0253* (2013.01); *A61M 2025/028* (2013.01)
USPC ........... 604/240; 604/181; 604/187; 604/192; 604/194

(58) Field of Classification Search
CPC ....... A61M 5/258; A61M 25/02; A61M 5/00; A61M 5/31
USPC .......................... 604/240, 181, 187, 192, 194
See application file for complete search history.

(56) References Cited

U.S. PATENT DOCUMENTS

| | | | |
|---|---|---|---|
| 4,488,545 A | 12/1984 | Shen | |
| 5,251,873 A * | 10/1993 | Atkinson et al. | ........... 251/149.1 |
| 5,833,213 A * | 11/1998 | Ryan | ........................... 251/149.1 |
| 7,455,663 B2 * | 11/2008 | Bikovsky | ....................... 604/240 |
| 2002/0161332 A1 * | 10/2002 | Ramey | ...................... 604/164.07 |
| 2007/0185441 A1 | 8/2007 | Fangrow, Jr. | |
| 2011/0160662 A1 | 6/2011 | Stout et al. | |
| 2012/0226239 A1 * | 9/2012 | Green | ........................... 604/192 |

FOREIGN PATENT DOCUMENTS

| | | |
|---|---|---|
| EP | 1 776 980 A1 | 4/2007 |
| EP | 2 364 738 A2 | 9/2011 |
| EP | 2 399 624 A1 | 12/2011 |
| EP | 2 433 663 A1 | 3/2012 |
| WO | 2006/062636 A1 | 6/2006 |
| WO | 2008/133702 A1 | 11/2008 |
| WO | 2011/089193 A2 | 7/2011 |
| WO | 2011/121023 A1 | 10/2011 |

\* cited by examiner

*Primary Examiner* — Scott Medway
(74) *Attorney, Agent, or Firm* — Jeanne Lukasavage; Craig Metcalf; Kirton McConkie

(57) ABSTRACT

A Luer securement device comprising a Luer adapter having a septum and a catheter hood, the Luer adapter further having a wedge seal for receiving a base portion of a catheter. The Luer securement device further includes an inserter body in which is slidably housed a catheter threader having a probe which is configured to advance a base portion of a catheter through the septum thereby seating the base portion of the catheter into the wedge seal of the Luer adapter as a tip portion of the catheter is inserted into a patient. The catheter threader further includes a needle adapter having a needle which is threaded through the probe and the catheter to assist in inserting the catheter into the patient. Following insertion of the catheter, the catheter threader is retracted within the inserter body thereby withdrawing the needle from the catheter and shielding a sharpened tip of the needle within at least one of the inserter body and the catheter threader. The inserter body is then detached from the Luer adapter and discarded.

20 Claims, 14 Drawing Sheets

INTEGRATED CATHETER SECUREMENT AND LUER ACCESS DEVICE

BACKGROUND OF THE INVENTION

This disclosure relates generally to catheters and Luer devices. More specifically, this disclosure discusses an integrated catheter securement and Luer access device that comprises an inserter body selectively coupled to a Luer adapter, wherein the inserter body advances and seats a catheter into the Luer adapter while simultaneously accessing the patient with the catheter.

As used herein, the term "Luer" is understood to describe and include any Luer taper or other system of small-scale fluid fittings used for making leak-free connections between a male-taper fitting and its mating female part on medical devices and/or equipment. A Luer device in accordance with the present invention may further include an integrated septum, whereby to provide selective access between two devices interconnected via a Luer fitting connection. Non-limiting examples of Luer fittings include "Luer-Lok," "Luer-Slip," and "Nexiva Closed IV Catheter" systems produced by Becton Dickenson, Inc.

Infusion therapy involves the administration of a fluid to a patient through a needle or catheter. It is generally prescribed when a patient's treatment cannot be treated effectively by oral medication. Typically, "infusion therapy" refers to procedures where a drug or other fluid is administered intravenously. However, the term also refers to situations where fluids are provided through other non-oral routes, such as intramuscular injections, subcutaneous injections, and epidural routes.

Intramuscular and subcutaneous injections place a bolus of fluid into the patient's tissue. The bolus slowly dissipates and is absorbed into the surrounding tissues thereby administering the medication or fluid to the patient over a period of time. The injection process generally requires steady control of the catheter and needle to ensure proper access while avoiding or minimizing injury to the patient. In emergency situations, such as in the back of a moving ambulance, a physician or other caregiver may be incapable of inserting a catheter into a patient due to excessive movement of the patient's surrounding. As such, the ambulance is required to stop to allow the caregiver a steady environment in which to insert the catheter. This creates an inconvenience to the caregiver and wastes valuable time that may be needed to save the life of the patient. Accordingly, there is a need in the art for a device which overcomes the difficulties and shortcomings associated with currently available technologies. The present disclosure discusses such a device.

BRIEF SUMMARY OF THE INVENTION

The present invention provides a Luer securement device which includes a Luer adapter having a first end which contains a septum and a second end which includes a catheter hood having a base for forming a secure interface with a body surface of a patient. The Luer adapter further includes a wedge seal interposed between the first and second ends. The wedge seal is provided to receive a base portion of a catheter which is inserted through the septum and into the wedge seal via a probe portion of a catheter threader. Once seated within the wedge seal, a fluid-tight seal is established between the catheter base and the wedge seal.

Some implementations of the present invention further include an inserter body which is selectively coupled to the Luer adapter. The inserter body slidably houses a catheter threader which includes a probe for contacting and advancing a catheter through the septum to seat a base portion of the catheter into the wedge seal.

The catheter threader further includes a needle adapter slidably housed within catheter threader. The needle adapter includes a needle having a sharpened tip which extends through the probe and the catheter such that the sharpened tip is exposed distally beyond a tip of the catheter to assist in inserting the catheter into a patient. In some instances, a distal spring is interposed between the catheter threader and the inserter body to provide a proximal compressive force between the two components. The Luer securement device further includes a proximal spring interposed between the catheter threader and the needle adapter to provide a distal compressive force between the two components.

Following insertion of the catheter into the patient, the proximal spring retracts the catheter adapter in a proximal direction thereby withdrawing and shielding the sharpened tip of the needle inside at least one of the inserter body and the probe portion of the catheter threader. The inserter body is then removed from the Luer adapter and discarded. The Luer adapter remains secured to the patient via an adhesive film. The Luer adapter maintains the position of the catheter within the patient and provides access to the catheter via the male Luer and septum of the Luer adapter.

BRIEF DESCRIPTION OF THE SEVERAL VIEWS OF THE DRAWINGS

In order that the manner in which the above-recited and other features and advantages of the invention are obtained and will be readily understood, a more particular description of the invention briefly described above will be rendered by reference to specific embodiments thereof, which are illustrated in the appended drawings. Understanding that these drawings depict only typical embodiments of the invention and are not, therefore, to be considered to be limiting of its scope, the invention will be described and explained with additional specificity and detail through the use of the accompanying drawings in which:

FIG. 4I illustrates a cross-section top view of a Luer securement device having a catheter threader positioned within an inserter body of the device, the device further having a needle adapter positioned in a third needle position in accordance with a representative embodiment of the present invention.

DETAILED DESCRIPTION OF THE INVENTION

Figure 1:
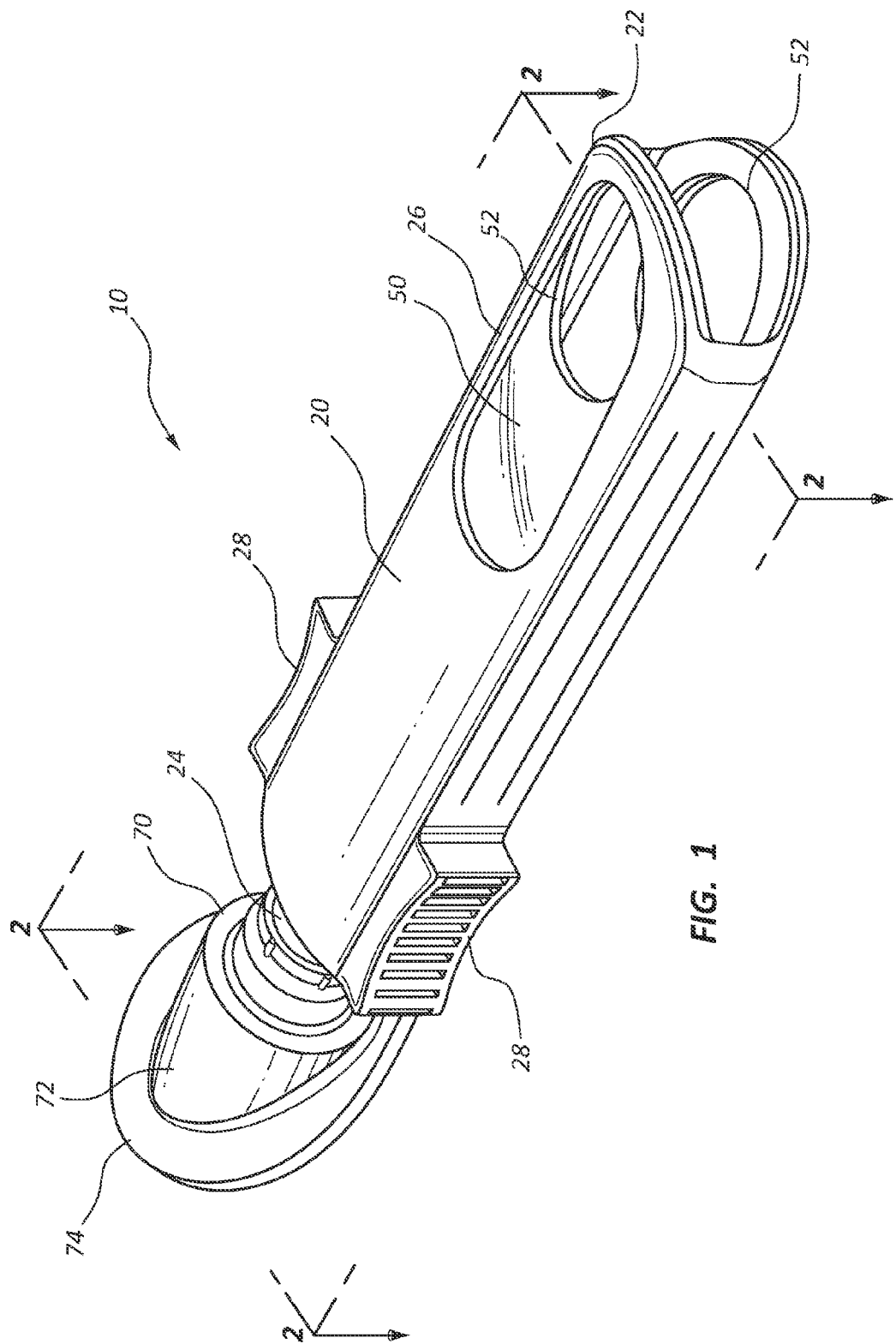
FIG. 1 illustrates a perspective view of a Luer securement device in accordance with a representative embodiment of the present invention.

The presently preferred embodiments of the described invention will be best understood by reference to the Figures, wherein like parts are designated by like numerals throughout. It will be readily understood that the components of the present invention, as generally described and illustrated in the accompanying Figures, could be arranged and designed in a wide variety of different configurations. Thus, the following more detailed description of some embodiments of the invention, as represented in the Figures, is not intended to limit the scope of the invention, as claimed, but is merely representative of some presently preferred embodiments of the invention.

Generally, the present invention relates to an integrated unit for securing a catheter and a Luer access device to a patient. In particular, some embodiments of the present invention provide a handheld device which includes an applicator or catheter inserter which is selectively coupled to a Luer adapter. In some instances, the Luer adapter comprises a hood made of a flexible polymer material which comprises a base configured to form an interface with a body surface of a patient. In some embodiments, the base of the Luer adapter further comprises an adhesive to secure and fix the location of the Luer adapter on the patient. Non-limiting examples of a compatible Luer adapter is provided in U.S. patent application Ser. No. 13/614,481, titled LUER SECUREMENT DEVICE, filed Sep. 13, 2012 by Stephen Bornhoft, which is incorporated herein by reference in its entirety.

The catheter inserter is coupled to the Luer adapter in a removable manner. Thus, following insertion of the catheter into the patient, the catheter inserter is selectively removed from the Luer adapter and discarded. The Luer adapter remains in place thereby allowing fluid access to the patient.

The embodiments of the present invention further include a catheter. The catheter of the present invention may include any type or style of catheter compatible with in vitro use. For example, in some instances the present invention includes a subcutaneous or intramuscular catheter. Accordingly, catheters compatible with the present invention may include flexible, polymer catheters and or rigid polymer or metallic catheters.

The applicator or catheter inserter comprises various components to facilitate the catheterization of the patient. In particular, the catheter inserter comprises a catheter threader which is slidably housed within the catheter inserter and which includes a probe configured to advance a catheter through a septum of the Luer device and into a patient. The catheter threader further includes a needle inserter or needle adapter which is slidably housed within the catheter threader and which includes a needle which extends through the probe of the catheter threader and through the cannula to assist in inserting the catheter into a patient. Once the catheter is inserted into the patient, the position of the catheter threader within the catheter inserter is retracted thereby withdrawing the needle from the catheter and shielding a sharpened tip of the needle within the catheter inserter.

The interconnected relationship between the Luer adapter and the catheter inserter provides a bridged connection between the catheter and the surface of the patient. In particular, the hood of the Luer adapter provides a stable, constant connection between the patient and the catheter thereby permitting catheterization of a patient in unstable surroundings or conditions. In other words, the hood of the Luer adapter provides a constant connection between the Luer securement device and the surface of the patient, such that a distance between the user's hand and the patient remains constant during catheterization. To provide a better understanding of the Luer securement device, the various integrated components of the device are described below in greater detail.

Referring now to FIG. 1, a perspective view of an assembled Luer securement device 10 is shown. In general, Luer securement device 10 comprises an applicator or inserter body 20 which is selectively coupled to a Luer adapter 70. Inserter body 20 comprises a hollow shell in which is slidably housed a catheter threader 50. Catheter threader 50 is slidably repositioned within inserter body 20 by the user to advance a catheter and needle through Luer adapter 70 and into a patient. Following catheterization, the needle is automatically retracted from the patient and Luer adapter 70 such that a sharpened tip of the needle is shielded within at least one of inserter body 20 and catheter threader 50. Inserter body 20 is then detached from Luer adapter 70 and discarded. Luer adapter 70 remains attached to the patient to provide access to the patient via the inserted catheter.

More specifically, in some embodiments Luer securement device 10 comprises an applicator or inserter body 20 having a proximal end 22 and a distal end 24. Inserter body 20 further comprises a hollow interior space in which is slidably housed a catheter threader 50. Inserter body 20 further comprises an access window 26 which is generally located at proximal end 22, and which provides user-access to catheter threader 50.

Catheter threader 50 further comprises a feature 52 which is configured to receive or accommodate a thumb or other finger of a user to slidably reposition catheter threader 50 within inserter body 20. For example, in some embodiments feature 52 comprises an aperture having a diameter sufficient to accommodate a user's thumb.

In some embodiments, the length of access window 26 is determined and selected based upon a desired or permitted length of travel for catheter threader 50 within inserter body 20. Thus, the distal and proximal limits of access window 26 dictate the maximum proximal and distal positions of catheter threader 50 within inserter body 20.

Inserter body 20 further comprises distal side grips 28 which are provided to assist the user in gripping distal end 24 of inserter body 20 between two adjacent fingers, for example, between the index and middle fingers of the hand. Thus, side grips 28 provide opposing surfaces which are configured to accommodate gripping of Luer securement device 10 and provide opposing surfaces against which adjacent fingers of the user may pull to facilitate the user in sliding catheter threader 50 within inserter body 20 via the user's thumb inserted into aperture 52. Accordingly, some embodiments of the present invention permit a user to hold and use Luer securement device 10 in a ported grip configuration, wherein a distal end of the device 10 is held between adjacent fingers of the user with the user's some being positioned in aperture 52. In some embodiments, side grips 28 further comprise a flexible or moldable material which conforms to support the user's grip. In other embodiments, side grips 28 comprise lateral extensions of inserter body 20 which provide gripping surfaces which are perpendicular to inserter body 20.

Luer securement device 10 further comprises a Luer adapter 70 which is selectively coupled to a distal end 24 of inserter body 20. Luer adapter 70 includes a hood 72 which comprises a flexible, elastomeric polymer material. Hood 72 further comprises a base 74 which is configured to form an interface with a body surface of a patient. In some embodiments, base 74 further comprises an adhesive whereby to secure and fix the position of Luer adapter 70 on the patient.

In some embodiments, Luer adapter 70 is threadedly coupled to distal end 24 of inserter body 20. For example, in some embodiments distal end 24 of inserter body 20 further comprises a set of female threads configured to threadedly receive a set of male threads of Luer adapter 70. Thus, a user may selectively remove inserter body 20 from Luer adapter 70 by unthreading the two components.

Figure 2:
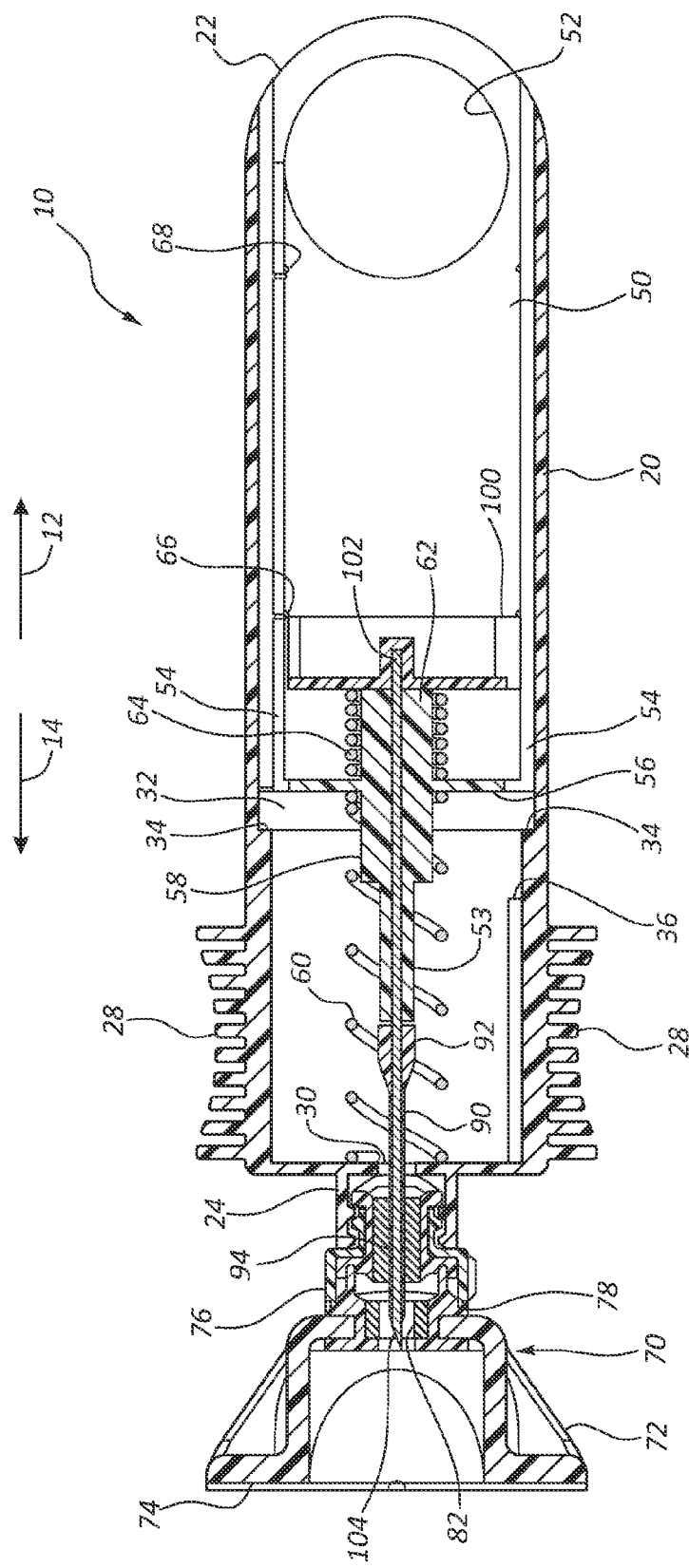
FIG. 2 illustrates a cross-section view of a Luer securement device in accordance with a representative embodiment of the present invention.

Referring now to FIG. 2, a cross-section view of Luer securement device 10 is shown prior to catheterization. In some embodiments, Luer adapter 70 comprises a male Luer 76 in which is housed a septum 80. Septum 80 further comprises a slit or other pathway through which a catheter 90 may be inserted. In some embodiments, the slit or pathway is preformed. In other embodiments, the slit or pathway is formed by advancing catheter 90 through septum 80.

A distal end of male Luer 76 further comprises a hood adapter 78 having a distal channel into which a proximal end of hood 72 is seated. Hood adapter 78 further includes a proximal end which forms an interface with septum 80. In some embodiments, the proximal end of hood adapter 78 wedges or otherwise captures a distal end of septum 80 between hood adapter 78 and an inner surface of male Luer 76.

Hood adapter 78 further comprises a middle channel in which is seated a wedge seal 82. Wedge seal 82 generally comprises a polymer material capable of forming a fluid-tight seal between hood adapter 78 and a base portion 92 of catheter 90.

As previously discussed, Luer adapter 70 is threadedly coupled to distal end 24 of inserter body 20. In some embodiments, distal end 24 comprises a nozzle having an inner surface which includes a threaded surface for threadedly receiving the threaded surface of male Luer 76. Distal end 24 further comprises a distal aperture 30 which is sized and configured to permit passage of catheter 90 and probe 53 of catheter threader 50.

Catheter threader 50 is slidably housed within interior space 32 of inserter body 20. In some embodiments, catheter threader 50 comprises an alignment channel 54 which is configured to receive and travel along an interior ridge 34 of inserter body 20 in proximal and distal directions 12 and 14, respectively. In some instances, catheter threader 50 comprises a plurality of alignment channels 54 which are provided to maintain proper alignment and position of catheter threader 50 within interior space 32 of inserter body 20.

Catheter threader 50 further comprises a probe 53 which extends distally from distal end 56. Probe 53 is sized and configured to form an interface with base portion 92 of catheter 90. For example, in some embodiments the outer diameter of probe 53 is approximately equal to the outer diameter of base portion 92 of catheter 90. As such, probe 53 is capable of advancing base portion 92 of catheter 90 through distal aperture 30 and through septum 80 to seat base portion 92 into wedge seal 82 of hood adapter 78.

Distal end 56 further comprises a distal protrusion 58 over which is seated a distal spring 60. Distal spring 60 provides compressive force between catheter threader 50 and inserter body 20 as catheter threader 50 is slid in distal direction 14. As such, distal spring 60 assists the user in sliding catheter threader 50 in proximal direction 12.

Distal end 56 further comprises a proximal protrusion 62 over which is seated a proximal spring 64. Proximal spring 64 provides compressive force between catheter threader 50 and needle adapter 100 when needle adapter 100 is in a distal or first needle position, as shown. In some embodiments, an inner surface of catheter threader 50 further comprises a stop feature 66 which maintains the first needle position of needle adapter 100 during the catheterization process. The first needle position is defined as the position of needle adapter 100 within catheter threader 50 wherein the sharpened tip 104 of needle 102 extends distally beyond the tip 94 of catheter 90.

When engaged by stop feature 66, needle adapter 100 travels with catheter threader 50 as catheter threader 50 is slid in distal direction 14. A sheer force between needle adapter 100 and stop feature 66 is selected to be greater than the compressive force of proximal spring 64 when needle adapter 100 is in the first needle position, thereby maintaining the first needle position of needle adapter 100. One having skill in the art will appreciate that stop feature 66 may include any mechanical feature which maintains the first needle position of needle adapter 100 with a force greater than the compressive force of proximal spring 64.

In some embodiments, interior space 32 further comprises a rigid boss 36 which is positioned and configured to pass through alignment channel 54 and contact needle adapter 100 as catheter threader 50 is slid in distal direction 14. Upon contact between boss 36 and needle adapter 100, the compressive force between boss 36 and needle adapter 100 increases as catheter threader continues to be slid in distal direction 14. At the point in which the compressive force between boss 36 and needle adapter 100 exceeds the sheer force between stop feature 66 and needle adapter 100, needle adapter 100 bypasses stop feature 66 in proximal direction 12. Once needle adapter 100 bypasses stop feature 66, the compressive force of proximal spring 64 pushes needle adapter 100 in proximal direction 12 thereby withdrawing needle 102 from catheter 90 and through septum 80.

Figure 3:
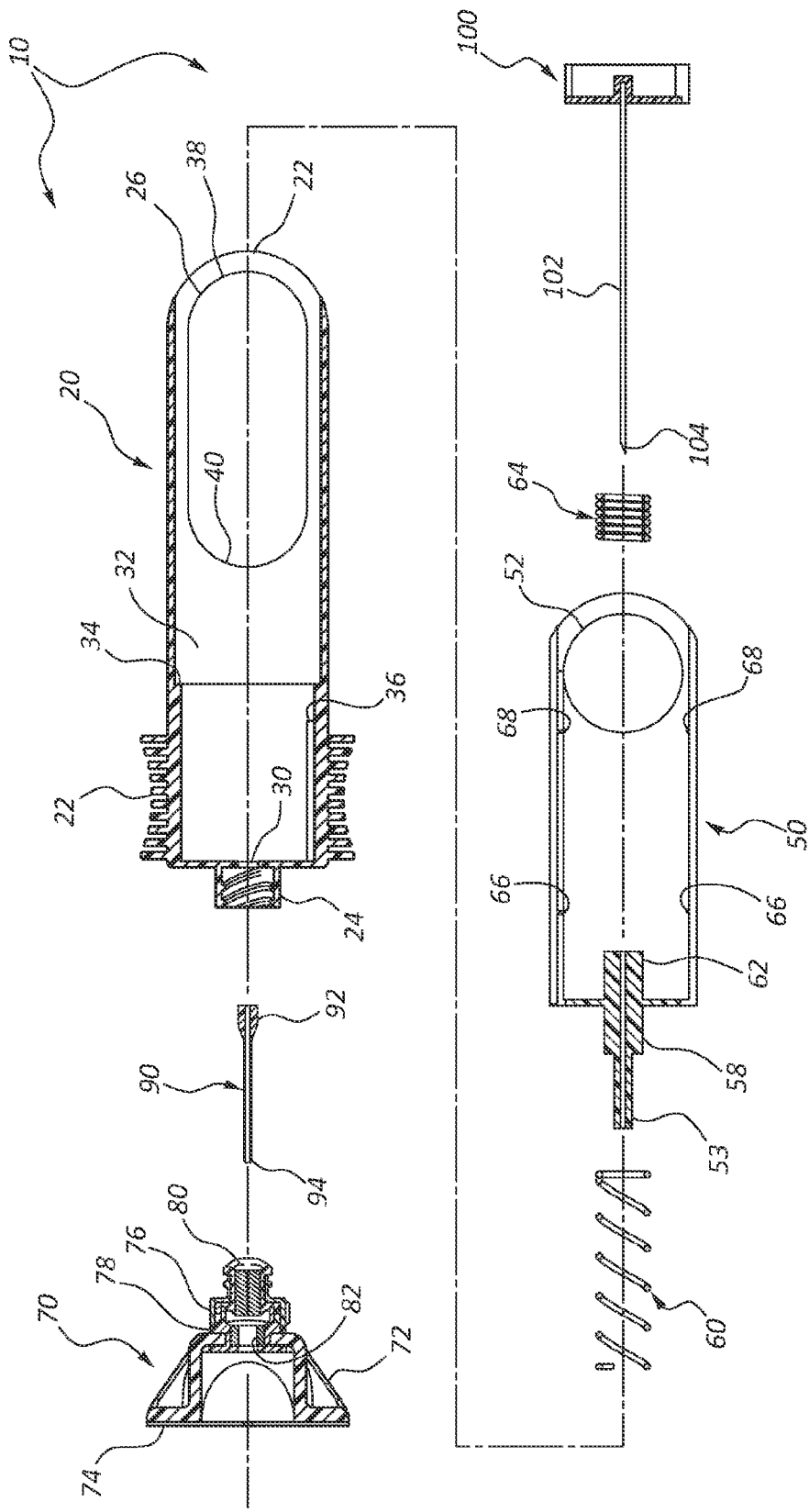
FIG. 3 illustrates a cross-section, exploded view of a Luer securement device in accordance with a representative embodiment of the present invention.
Figure 4A:
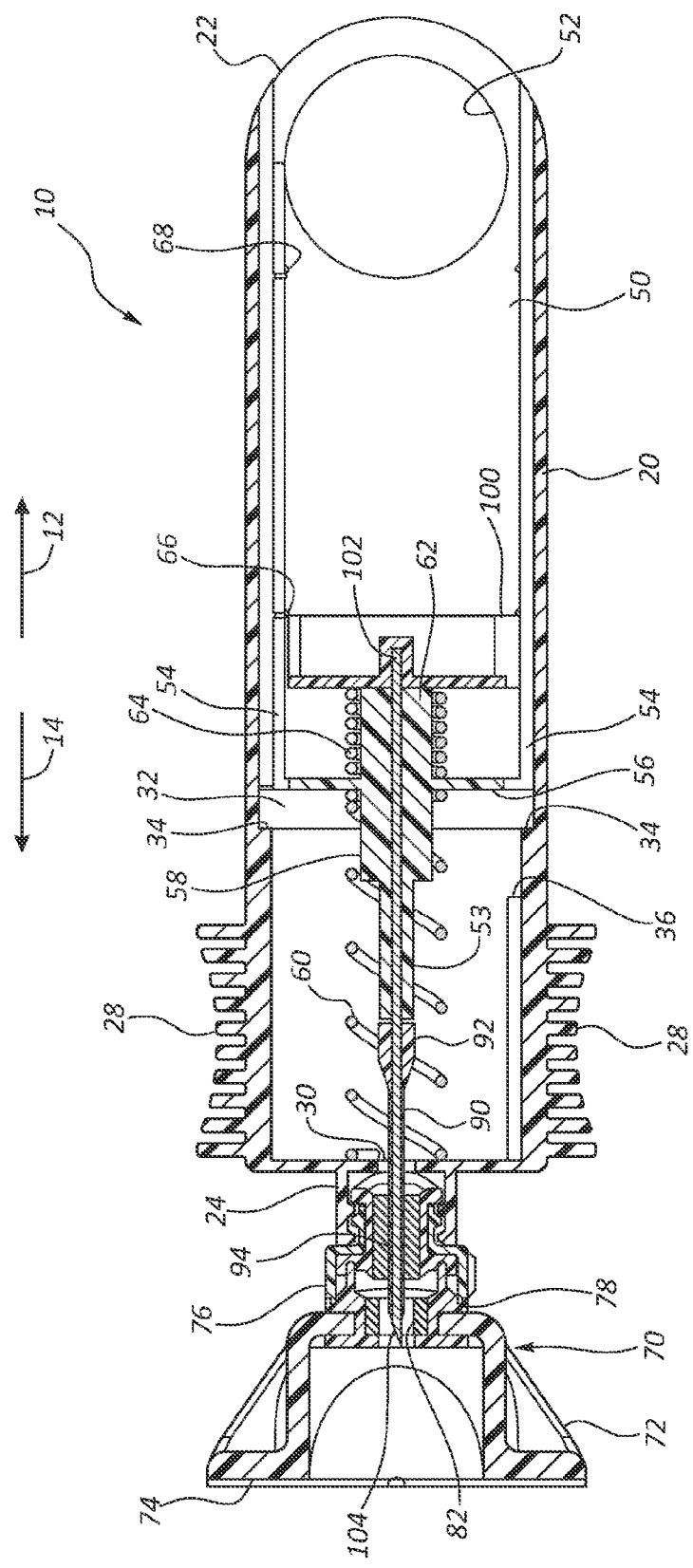
FIG. 4A illustrates a cross-section top view of a Luer securement device having a catheter threader in a first position and a needle adapter in a first needle position in accordance with a representative embodiment of the present invention.

Referring generally to FIGS. 3-4I, a cross-section view of Luer securement device 10 is shown at various stages of activation or use. For example, FIG. 4A shows Luer securement device 10 prior to activation, while FIG. 4I shows Luer securement device 10 following use. Accordingly, the process of insertion is shown sequentially from FIG. 4A to FIG. 4I, wherein the structural features of each component is clearly shown and isolated in FIG. 3.

The length of access window 26 is selected to limit movement of catheter threader 50 between a first position and a second position. The first position is characterized by aperture 52 of catheter threader 50 being aligned with the proximal end 38 of access window 26, as shown in FIG. 4A. The second position is characterized by aperture 52 being aligned with the distal end 40 of access window 26, as shown in FIG. 4E.

With continued reference to FIG. 4A, the first position is further characterized by the position of sharpened tip 104 of needle 102 with respect to tip 94 of catheter 90 and septum 80. In particular, in the first position sharpened tip 104 extends distally beyond tip 94 and is positioned distally to septum 80. As such, sharpened tip 104 and catheter 90 may be inserted into the patient without causing damage to septum 80, as sharpened tip 104 is not required to pass through septum 80 during catheterization. Accordingly, the placement of proximal end 38 of access window 26 is selected to position the interface between probe 53 and base portion 92 of catheter 90 such that tip 94 of catheter 90 extends through septum 80.

Figure 4B:
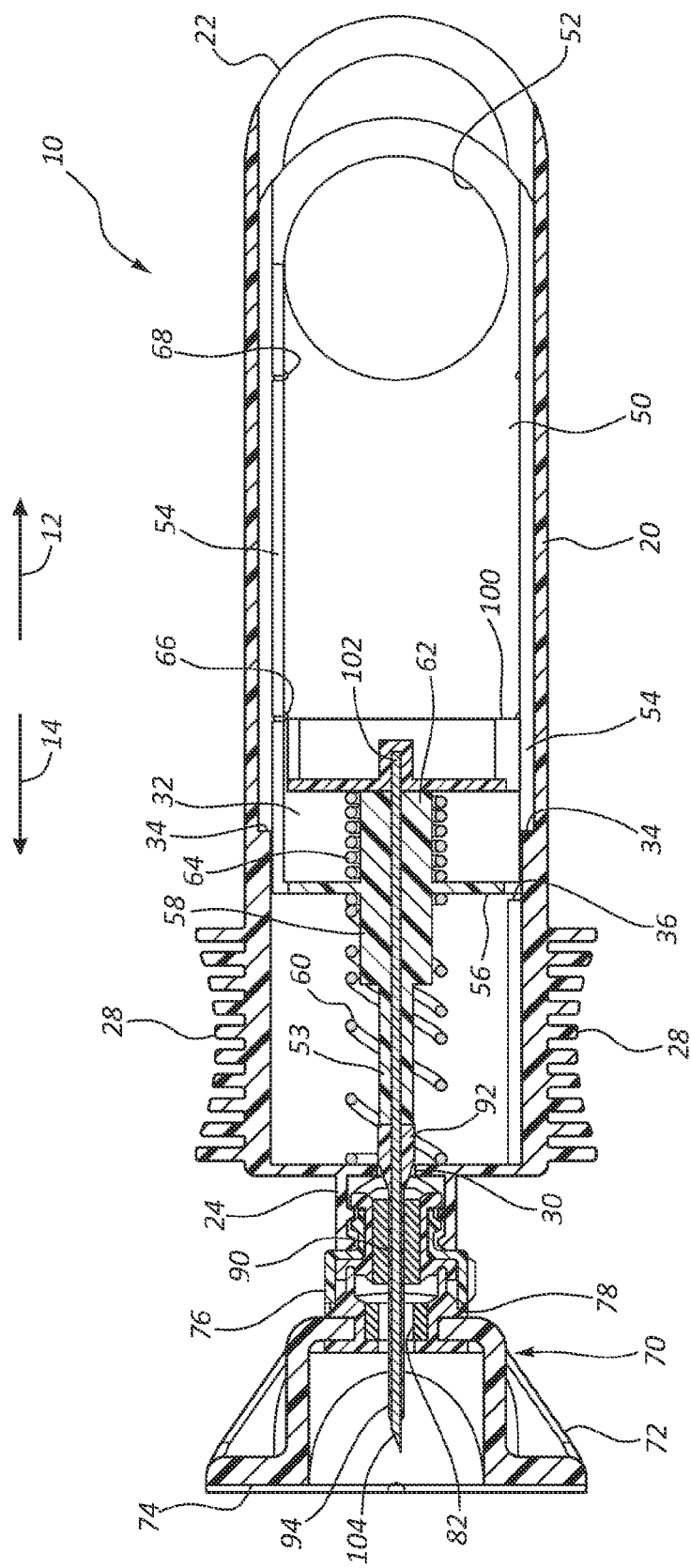
FIG. 4B illustrates a cross-section top view of a Luer securement device having a catheter threader being displaced from a first position and moving towards a second position, the device further having a needle adapter in a first needle position in accordance with a representative embodiment of the present invention.
Figure 4C:
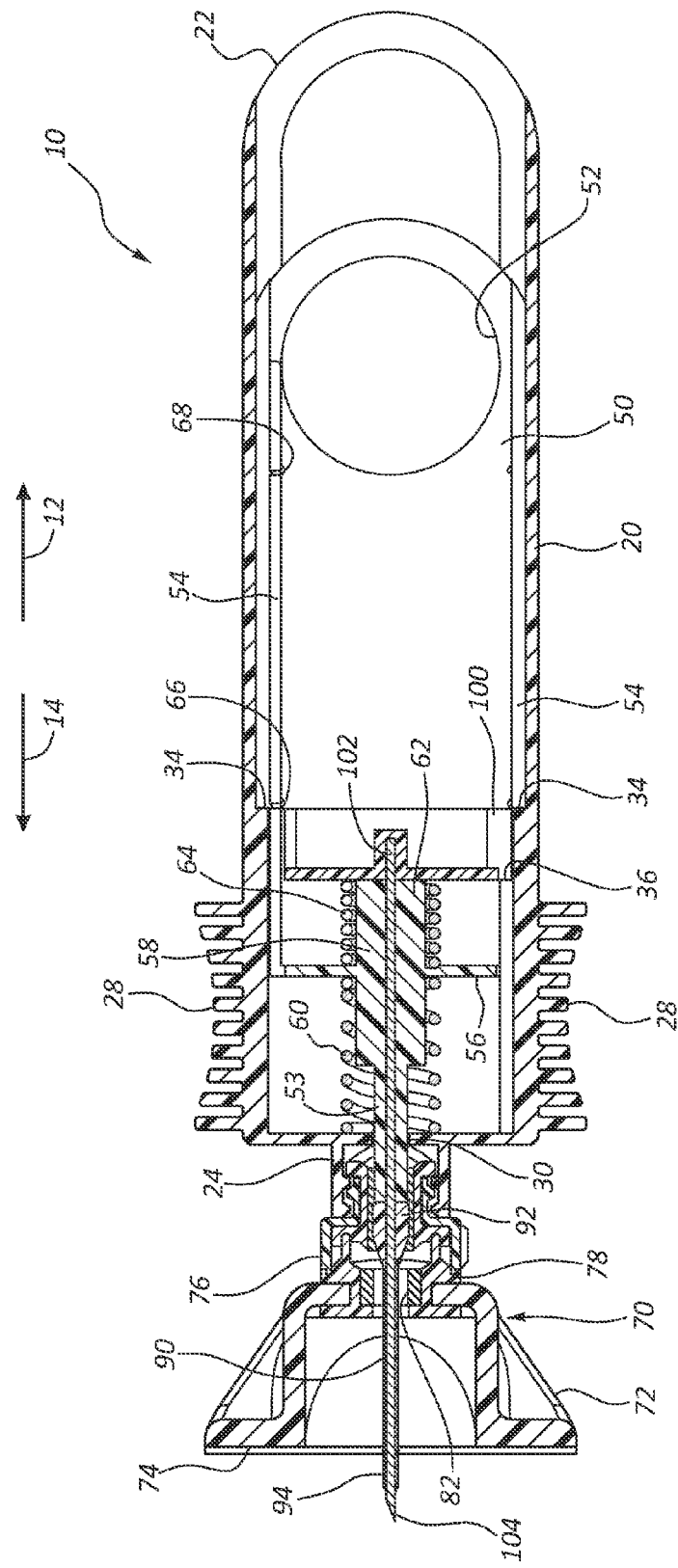
FIG. 4C illustrates a cross-section top view of a Luer securement device having a catheter threader positioned between a first position and a second position, the device further having a needle adapter in contact with a boss of the inserter body in accordance with a representative embodiment of the present invention.
Figure 4D:
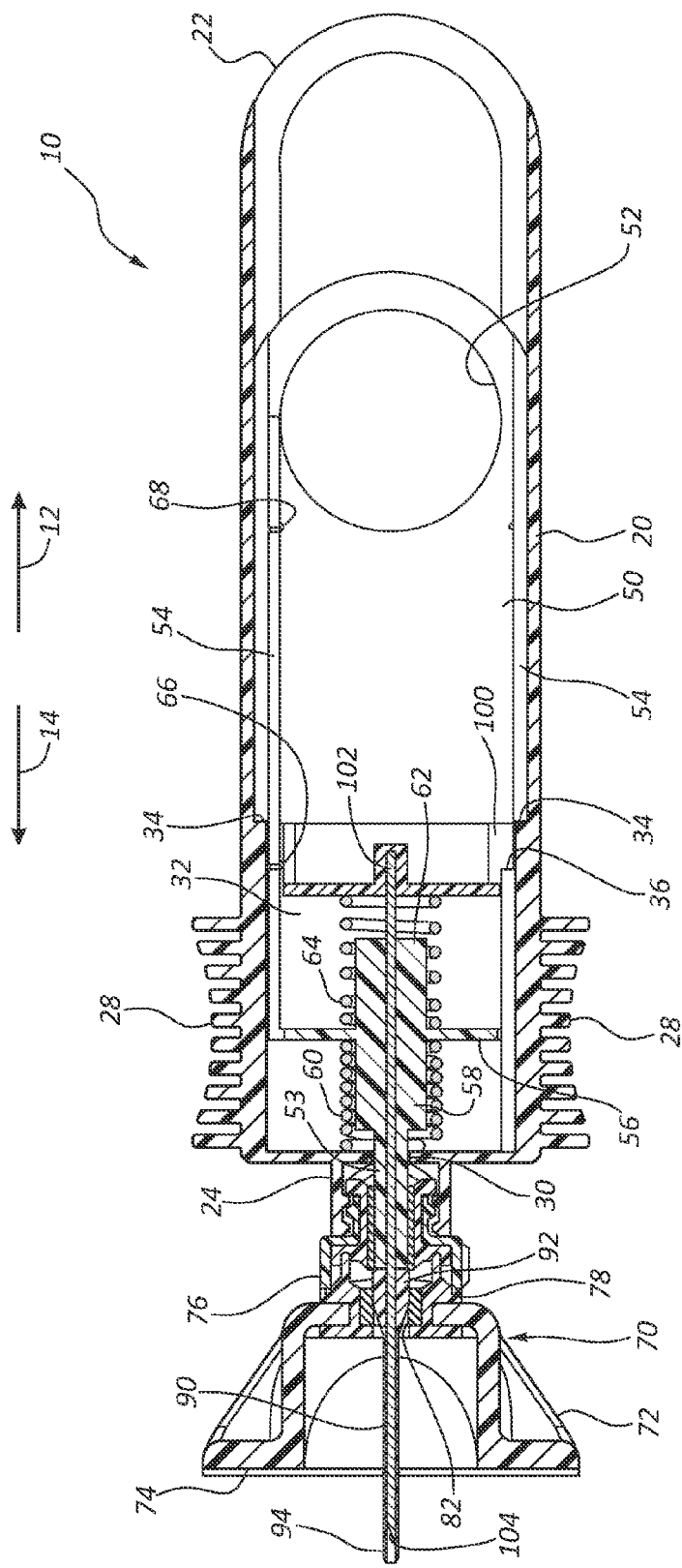
FIG. 4D illustrates a cross-section top view of a Luer securement device having a catheter threader positioned between a first position and a second position, the device further having a needle adapter in a second needle position in accordance with a representative embodiment of the present invention.
Figure 4E:
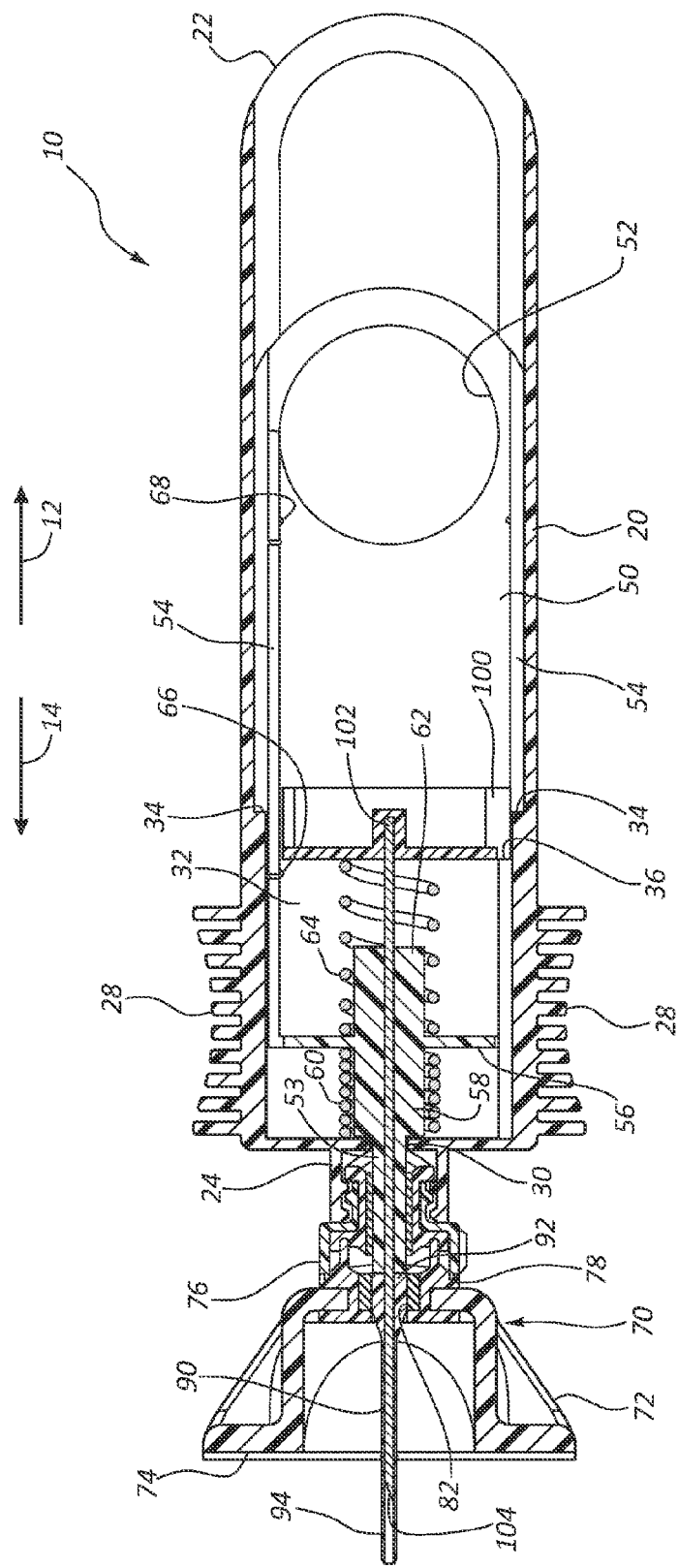
FIG. 4E illustrates a cross-section top view of a Luer securement device having a catheter threader positioned in a second position, the device further having a needle adapter positioned between a second needle position and a third needle position in accordance with a representative embodiment of the present invention.
Figure 4F:
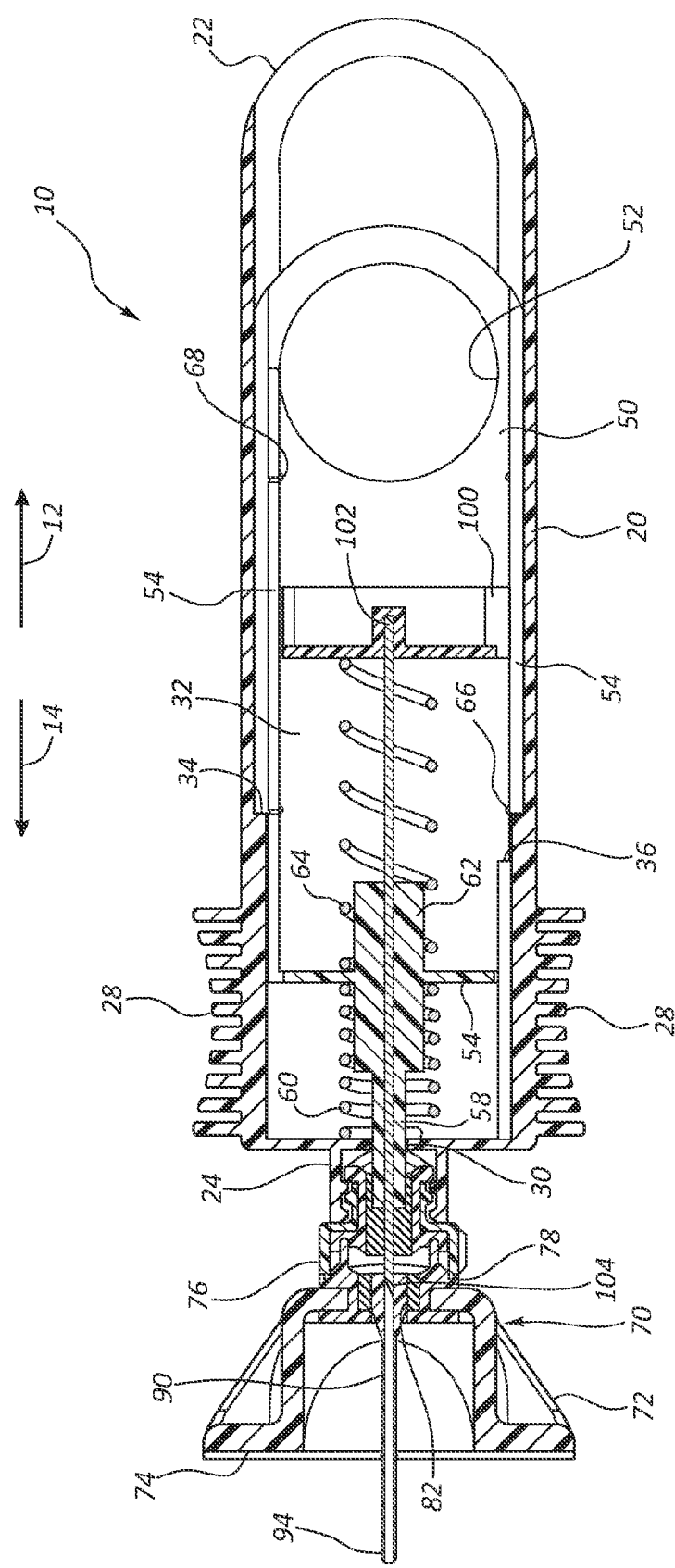
FIG. 4F illustrates a cross-section top view of a Luer securement device having a catheter threader in a second position, the device further having a needle adapter positioned between a second needle position and a third needle position in accordance with a representative embodiment of the present invention.
Figure 4G:
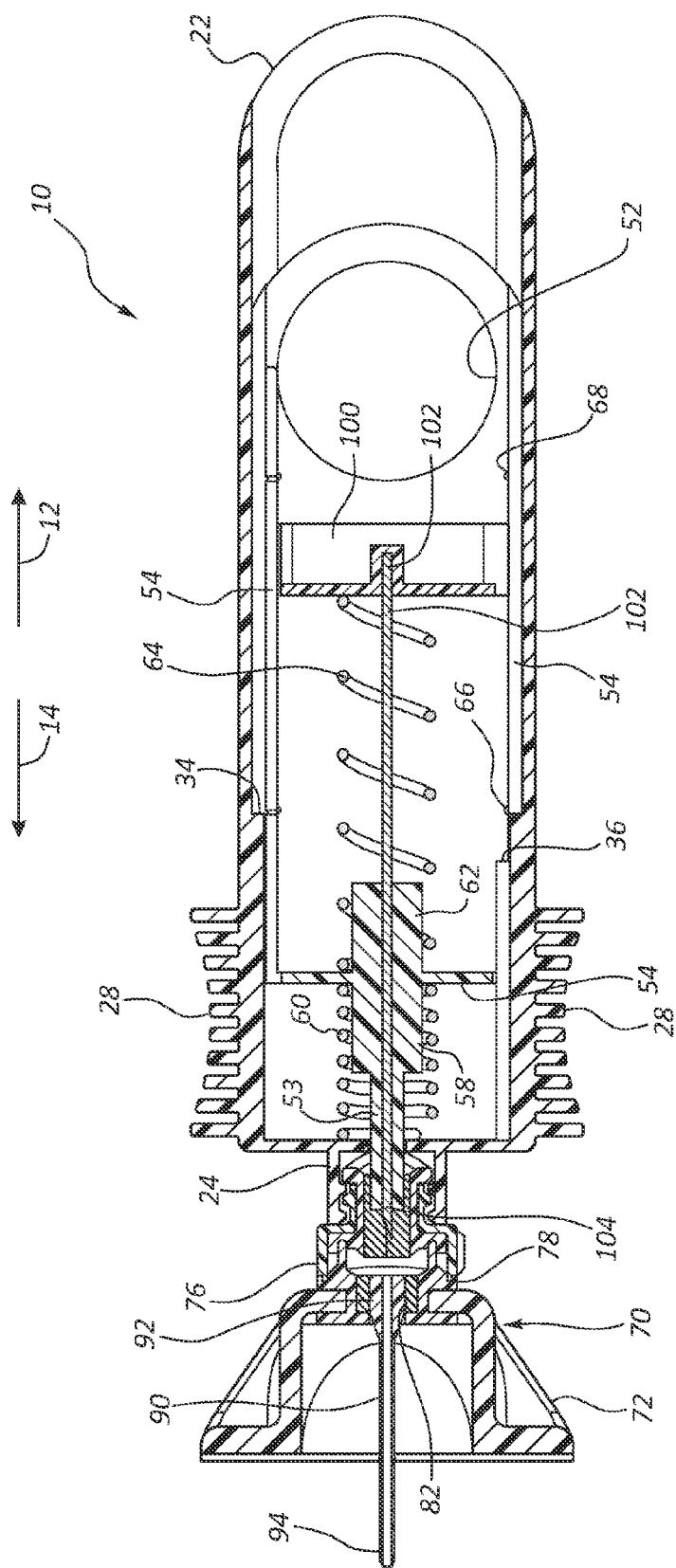
FIG. 4G illustrates a cross-section top view of a Luer securement device having a catheter threader in a second position, the device further having a needle adapter positioned between a second needle position and a third needle position in accordance with a representative embodiment of the present invention.
Figure 4H:
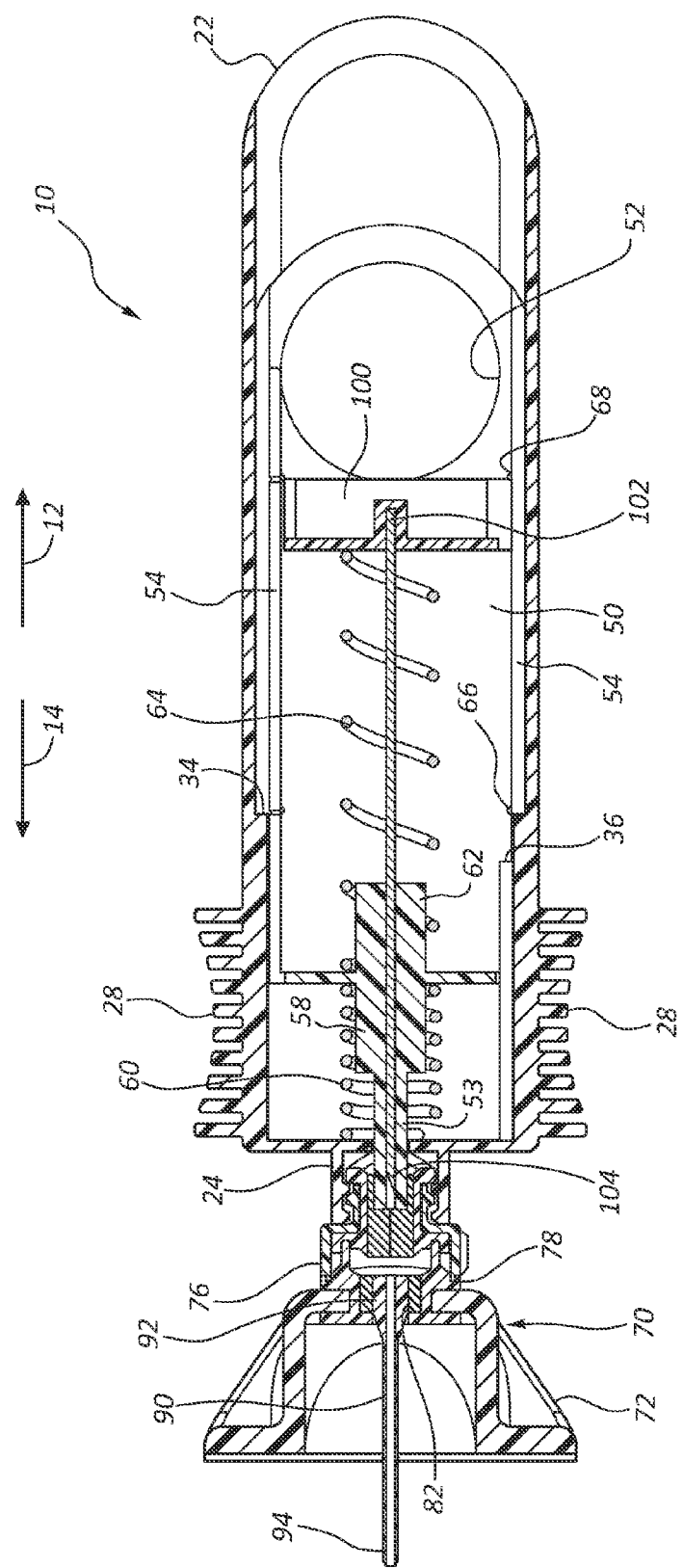
FIG. 4H illustrates a cross-section top view of a Luer securement device having a catheter threader and a second position, the device further having a needle adapter positioned between a second needle position and a third needle position in accordance with a representative embodiment of the present invention.
Figure 41:
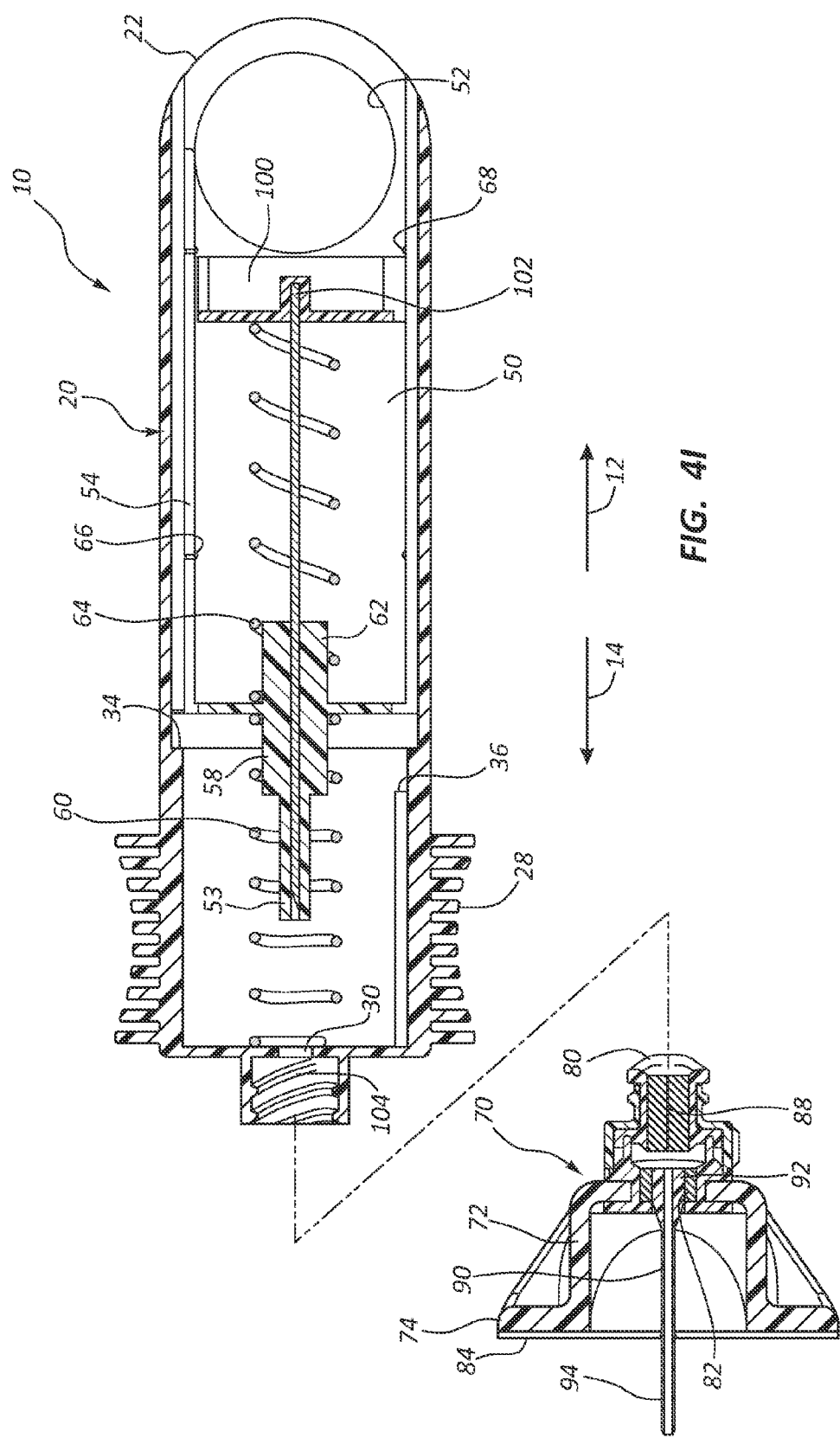

Similarly, the second position is characterized by the position of base portion 92 of catheter 90 with respect to wedge seal 82, as shown in FIG. 4E. In particular, in the second position base portion 92 is fully seated into wedge seal 82. Thus, the placement of distal end 40 of access window 26 is selected to limit distal sliding of catheter threader 50 such that base portion 92 of catheter 90 is fully seated into wedge seal 82.

With reference to FIGS. 4B and 4C, as catheter threader 50 is slid in distal direction 14, boss 36 contacts needle adapter 100 thereby halting the distal movement of needle adapter 100, and consequently halting the distal movement of sharpened tip 104 of needle 102 resulting in the configuration shown in FIG. 4C. Accordingly, the position of boss 36 is selected to limit the distal movement of needle adapter 100. In particular, the position of boss 36 is selected to halt distal movement of needle adapter 100 following insertion of sharpened tip 104 into the patient. Once halted, catheter threader 50 is permitted to continue sliding distally thereby advancing catheter tip 94 into the patient while sharpened tip 104 remains stationary, as shown in FIGS. 4D and 4E. Upon additional sliding or advancement of catheter threader 50 in distal direction 14, catheter tip 94 advances in distal direction 14 thereby withdrawing or shielding sharpened tip 104 within catheter 90. Thus, boss 36 is positioned to limit or halt distal movement of needle adapter 100 prior to catheter threader 50 fully attaining the second position.

As previously discussed, stop features 66 temporarily interlock catheter adapter 100 and catheter threader 50. Thus, when catheter threader 50 is in the first position, needle adapter 100 is in a first needle position, as shown in FIGS. 4A-4C. The first needle position is characterized by the position of sharpened tip 104 with respect to catheter tip 94. In particular, the first needle position is characterized by sharpened tip 104 of needle 102 extending distally beyond catheter tip 94. Thus, first needle position ensures that sharpened tip 104 is exposed to assist in providing catheter 90 with access to the patient.

As catheter threader 50 moves distally from the first position towards the second position, needle adapter 100 remains in the first needle position until rigid boss 36 contacts needle adapter 100, shown in FIGS. 4D-4G. When this contact occurs, probe 53 continues to advance catheter 90 distally thereby withdrawing sharpened tip 104 into catheter 90, as shown in FIGS. 4D-4G. Accordingly, a second needle position is characterized by contact between rigid boss 36 and needle adapter 100, wherein sharpened tip 104 is withdrawn proximally into catheter 90.

Once needle adapter 100 bypasses stop features 66, needle adapter 100 is biased proximally via proximal spring 64, thereby causing needle adapter 100 to travel from the second needle position to a third needle position, as shown in FIGS. 4E-4H. The third needle position is characterized by the position of sharpened tip 104 with respect to distal end 24 of inserter body 20. In particular, the third needle position results in sharpened tip 104 being positioned within interior space 32 of inserter body 20, as shown in FIG. 4I. Alternatively, in some embodiments the third needle position results in sharpened tip 104 being positioned within probe 53 of catheter threader 50.

With reference to FIGS. 4E-4H, as needle 102 is withdrawn or retracted in proximal direction 12, the outer surface of needle 102 is wiped clean by passing through septum 80. As such, blood or other fluid on needle 102 is removed prior to being shielded within inserter body 20. In some embodiments, the drag force of slit 88 of septum 80 on the outer surface of needle 102 is greater than the compressive force of proximal spring 64. As such, the position of needle adapter 100 remains stationary against boss 36 until inserter body 20 is disconnected from Luer adapter 70 and moved in proximal direction 12. As inserter body 20 is moved in proximal direction 12, needle 102 is drawn through slit 88 of septum 80 thereby cleaning the outer surface of needle 102. When sharpened tip 104 clears slit 88, the compressive force of proximal spring 64 is released thereby rapidly withdrawing sharpened tip 104 into probe 53 of catheter threader 50, as shown in FIG. 4I.

In some embodiments, catheter threader 50 further comprises one or more proximal stop features 68. Proximal stop features 68 are provided to limit proximal movement of needle adapter 100 within catheter threader 50. Accordingly, in some embodiments third needle position is defined by contact between needle adapter 100 and proximal stop features 68, wherein the third needle position shields sharpened tip 104 within at least one of inserter body 20 and catheter threader 50, as shown in FIG. 4I. Thus, as needle adapter 100 is slid proximally 12 by proximal spring 64, needle adapter 100 is prevented from exiting catheter threader 50 by contacting proximal stop features 68.

Figure 5:
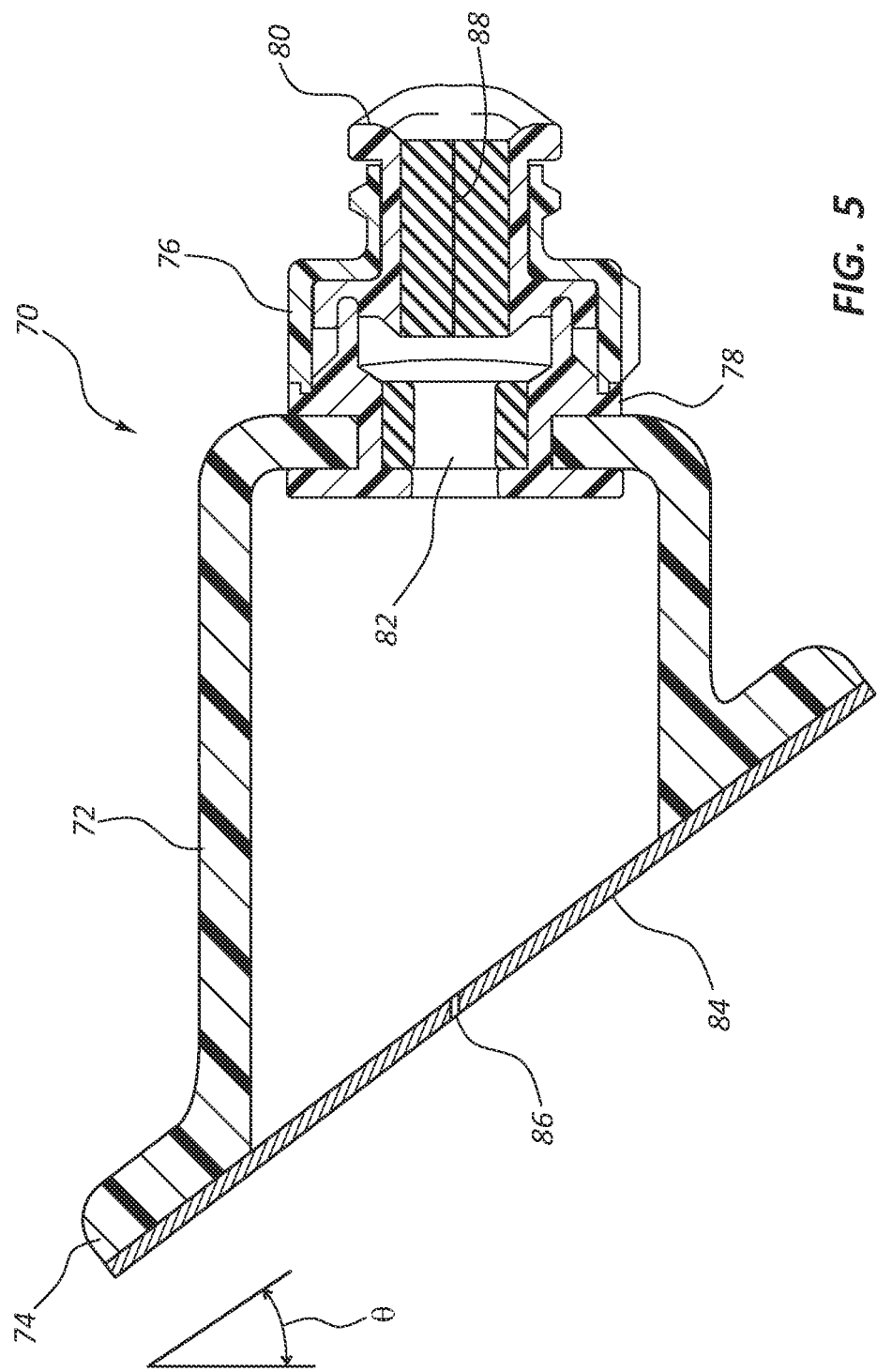
FIG. 5 illustrates a cross-section view of a Luer adapter in accordance with a representative embodiment of the present invention.

Referring now to FIG. 5, a cross-section side view of Luer adapter 70 is shown. In some embodiments, base 74 of hood 72 is angled to facilitate insertion of catheter 90 into the patient. The angle of base 74 may be selected based upon an optimal angle of insertion for catheter 90. For example, in some embodiments base 74 of hood 72 comprises an angle θ of approximately 30-45°. In other embodiments, angle θ comprises approximately 90°.

As previously discussed, in some embodiments base 74 further comprises an adhesive layer or film 84 which encloses the distal end of hood 72. Adhesive film 84 is applied to a body surface of a patient to secure and maintain the position of Luer adapter 70 on the patient. In some embodiments, adhesive film 84 further comprises a non-adhesive outer covering (not shown) which is removed by a user to expose adhesive film 84 prior to applying Luer adapter 70 to the patient's body. Adhesive film 84 further comprises an insertion target 86 in concentric alignment with wedge seal 82 and slit 88 of septum 80. Thus, as catheter 90 and needle 102 are advanced through septum 80 and hood 72, tip portion 94 and sharpened tip 104 pass through adhesive film 84 to contact the patient. In some embodiments, insertion target 86 further comprises a contrasting color whereby to serve as a visual marker for aligning insertion target 86 with an anatomical feature of the patient. For example, in some instances insertion target 86 is visually aligned to avoid piercing a vein.

Figure 6:
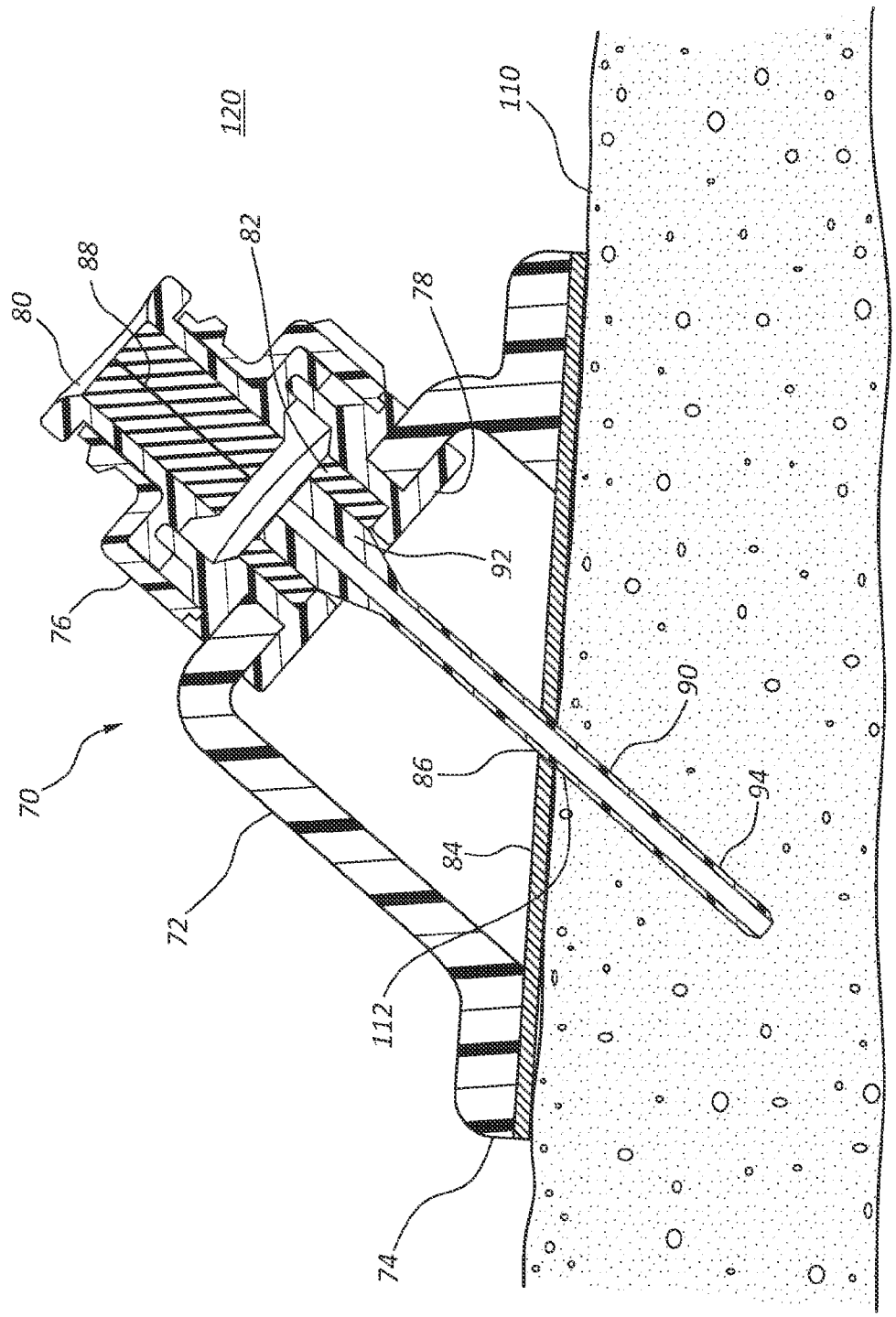
FIG. 6 illustrates a cross-section view of a Luer adapter and catheter inserted into a patient in accordance with a representative embodiment of the present invention.

Adhesive film 84 and hood 72 further provide a blood barrier between the patient 110 and an exterior environment 120, as shown in FIG. 6. For example, during catheterization blood may escape or leak from the insertion site 112 through adhesive film 84. The enclosed nature of hood 72 and adhesive film 84 captures any blood or other fluids thereby preventing undesirable exposure to the user. Wedge seal 82 further provides a fluid-tight seal between the base portion 92 of catheter 90 and hood adapter 78 thereby preventing blood from bypassing male Luer 76. Accordingly, once inserted into a patient 110, Luer adapter 70 provides a fluid-tight, enclosed system which is selectively accessible via slit 88 of septum 80.

The present invention may be embodied in other specific forms without departing from its structures, methods, or other essential characteristics as broadly described herein and claimed hereinafter. All of the described embodiments and examples are to be considered in any and all respects as illustrative only, and not restrictive. The scope of the invention is, therefore, indicated by the appended claims, rather than by the foregoing description. All changes that come within the meaning and range of equivalency of the claims are to be embraced within their scope.

The invention claimed is:

1. A securement device, comprising:
   an adapter having a first end comprising a septum and a second end comprising a catheter hood having a base, the adapter further comprising a wedge seal interposed between the first and second ends;
   an inserter body having a distal end for receiving the first end of the adapter;
   a catheter threader slidably housed within the inserter body, the catheter threader having a probe for contacting a base portion of a catheter, the probe being configured to advance the base portion of the catheter through the septum of the adapter and into the wedge seal, the wedge seal being configured to retain the catheter and form a fluid-tight seal between the base portion and the wedge seal, the probe further having an aperture providing a pathway through the probe;
   a needle adapter slidably housed within the catheter threader and including a needle which extends through the aperture of the probe and the catheter to assist in inserting the catheter into a patient; and
   at least one spring positioned within the catheter threader distal to the needle adapter.

2. The device of claim 1, wherein a proximal end of the catheter threader further comprises an opening into which a user's thumb can be inserted to slide the catheter threader within the inserter body.

3. The device of claim 2, wherein the inserter body further comprises an access window to permit a user to access the opening of the catheter threader, the access window having a greater longitudinal length than the opening of the catheter threader.

4. The device of claim 1, the catheter threader being slidably moveable within the inserter body from a first position to a second position, wherein when in the first position, the probe and the base portion of the catheter are positioned within the inserter body, and when in the second position, the probe is at least partially positioned within the septum of the adapter, and the base portion of the catheter is seated within the wedge seal.

5. The device of claim 4, the needle adapter being slidably moveable within the catheter threader from a first needle position, to a second needle position, to a third needle position, wherein when in the first needle position a sharpened tip of the needle extends distally beyond a tip of the catheter, and when in the second needle position the sharpened tip of the needle is withdrawn into the tip of the catheter, and when in the third needle position the sharpened tip of the needle is entirely withdrawn from the catheter and positioned within at least the catheter threader and the inserter body.

6. The device of claim 5, wherein the needle adapter is in the first needle position as the catheter threader moves from the first position to the second position, the needle adapter is in the second needle position when the catheter threader is in the second position, and the needle adapter moves from the second needle position to the third needle position as the catheter threader moves from the second position to the first position.

7. The device of claim 1, wherein the base further comprises an external adhesive layer.

8. The device of claim 1, wherein the at least one spring comprises a distal spring interposed between an outer surface of the catheter threader and an inner surface of the inserter body, and a proximal spring interposed between an inner surface of the catheter threader and the needle adapter.

9. The device of claim 7, wherein the external adhesive layer further comprises a target in concentric alignment with a pathway through the septum and the aperture of the probe.

10. The device of claim 9, wherein the sharpened tip of the needle and the tip of the catheter pass through the adhesive layer as the catheter threader is moved from the first position to the second position.

11. A catheter securement system, comprising:
   an adapter having a first end comprising a septum and a second end comprising a catheter hood having a base, the adapter further comprising a wedge seal interposed between the first and second ends;
   an inserter body removably coupled to the adapter, the inserter body having an interior space for slidably housing a catheter threader, the catheter threader having a probe configured to contact and advance a base portion of a catheter through the septum of the adapter, wherein the base portion of the catheter is seated in the wedge seal in a fluid-tight manner, the inserter further having an access window whereby a user may access the catheter threader to slide the catheter threader within the interior space of the inserter body from a first position to a second position;
   a needle adapter slidably housed within an interior space of the catheter threader and including an needle which extends through an aperture of the probe and the catheter to assist in inserting the catheter into a patient, wherein the catheter is inserted and advanced into a patient as the catheter threader is slid from the first position to the second position, the base portion of the catheter further being seated within the wedge seal as the catheter threader is slid from the first position to the second position, and wherein a sharpened tip of the needle is withdrawn from the catheter and into at least one of the inserter body and the catheter threader as the catheter threader is slid from the second position to the first position; and at least one spring positioned within the catheter threader distal to the needle adapter.

12. The system of claim 11, wherein a proximal end of the catheter threader further comprises a feature for receiving a user's thumb, wherein the feature is contained within the inserter body and permits a user to slide the catheter threader within the inserter body by sliding the user's thumb within the inserter body.

13. The system of claim 12, wherein the feature comprises an aperture.

14. The system of claim 12, wherein the inserter body further comprises an access window through which a user may access the feature of the catheter threader.

15. The system of claim 11, wherein the catheter threader is slidably movable within the interior space of the inserter body from a first position to a second position, wherein when in the first position, the probe and the base portion of the catheter are positioned within the interior space of the inserter body, and when in the second position, the probe is at least partially positioned within the septum of the adapter, and the base portion of the catheter is seated within the wedge seal.

16. The system of claim 15, wherein the needle adapter is slidably movable within the interior space of the catheter threader from a first needle position, to a second needle position, to a third needle position, wherein when in the first needle position a sharpened tip of the needle extends distally beyond a tip of the catheter, and when in the second needle position the sharpened tip of the needle is withdrawn into the tip of the catheter, and when in the third needle position the sharpened tip of the needle is entirely withdrawn from the catheter and positioned within at least the interior space of the catheter threader and the interior space of the inserter body.

17. The system of claim 16, wherein the needle adapter is in the first needle position as the catheter threader moves from the first position towards the second position, and the needle adapter moves from the second needle position to the third needle position when the catheter threader is in the second position.

18. The system of claim 11, wherein the adapter further comprises an adhesive layer that includes a target in concentric alignment with a pathway through the septum and the aperture of the probe.

19. The system of claim 18, wherein the sharpened tip of the needle and the tip of the catheter pass through the adhesive layer as the catheter threader is moved from the first position to the second position.

20. The system of claim 11, wherein the at least one spring comprises a distal spring interposedly positioned between an outer surface of the catheter threader and an inner surface of the inserter body, and a proximal spring interposedly positioned between an inner surface of the catheter threader and the needle adapter.

* * * * *